Figure 1:
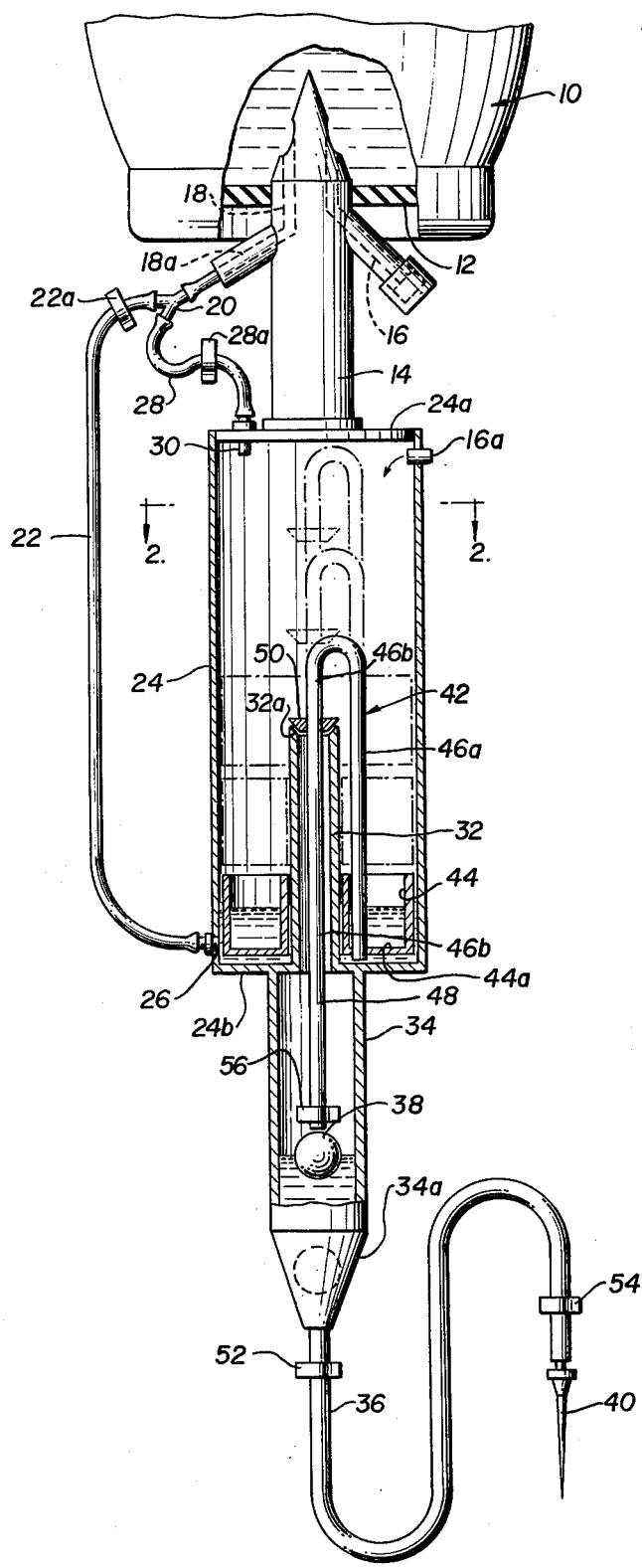

United States Patent [19]

Howell

[11] 4,099,527
[45] Jul. 11, 1978

[54] PARENTERAL FLUID ADMINISTRATION SETS

[76] Inventor: William L. Howell, 3615 Macomb St. NW., Washington, D.C. 20016

[21] Appl. No.: 778,118

[22] Filed: Mar. 16, 1977

Related U.S. Application Data

[63] Continuation-in-part of Ser. No. 675,242, Apr. 8, 1976, abandoned.

[51] Int. Cl.² ............................................. A61M 5/16
[52] U.S. Cl. ............................. 128/214 C; 128/228; 137/135; 222/416
[58] Field of Search ............ 128/214 R, 214 C, 214.2, 128/227, 228; 222/416; 137/129, 131, 135, 142

[56] References Cited

U.S. PATENT DOCUMENTS

| | | | |
|---|---|---|---|
| 2,640,358 | 6/1953 | McClure et al. | 222/416 X |
| 2,648,333 | 8/1953 | Cutter | 128/214 C |
| 3,625,211 | 12/1971 | Butler | 128/214 C |
| 3,938,539 | 2/1976 | Strouth et al. | 128/214 C X |
| 3,949,745 | 4/1976 | Howell | 128/214 C |
| 3,965,895 | 6/1976 | Dabney | 128/214 C |
| 3,989,043 | 11/1976 | Dimeff | 128/214 C |

FOREIGN PATENT DOCUMENTS

21,724  9/1947  Finland ................. 137/135

*Primary Examiner*—Dalton L. Truluck
*Attorney, Agent, or Firm*—J. Harold Kilcoyne

[57] ABSTRACT

A parenteral fluid administration set characterized by a floating siphon operating within a deformable-reformable, plastic-walled, generally cylindrical flow regulator having a normally open-ended overflow tube extending uprightly therein from its bottom end-wall, being thus generally similar both structurally and to a degree functionally to the fluid administration set disclosed in my copending application Ser. No. 608,576 filed Aug. 28, 1975, (now U.S. Pat. No. 3,949,745 dated Apr. 13, 1976) but featuring means whereby the siphon may be primed to initiate fluid flow in controlled amount through the longer leg of the siphon more simply end effectively than by the siphon priming means according to my aforesaid prior-filed application.

10 Claims, 4 Drawing Figures

U.S. Patent July 11, 1978 Sheet 2 of 2 4,099,527
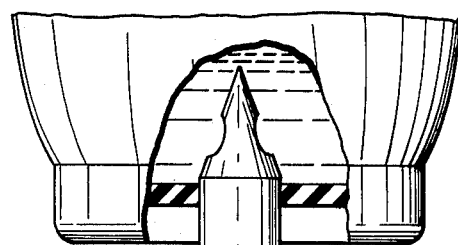
FIG. 3
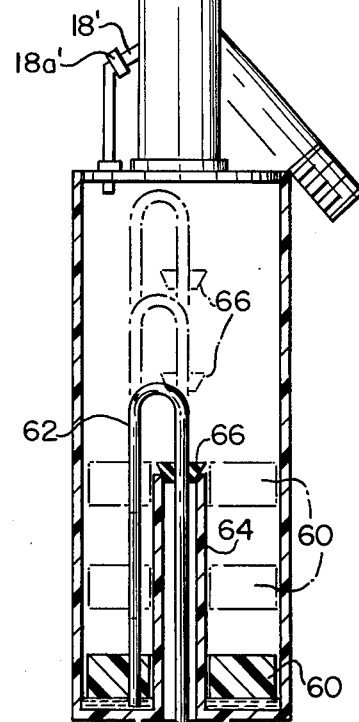
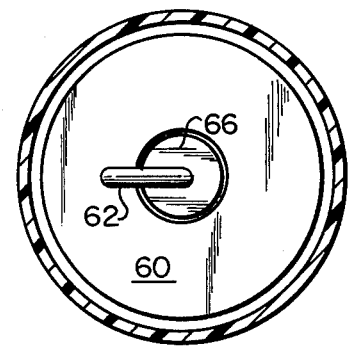
FIG. 4
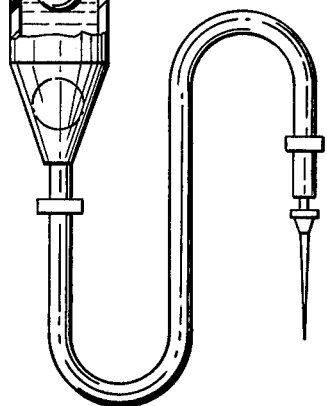

PARENTERAL FLUID ADMINISTRATION SETS

HISTORY OF THE PRESENT APPLICATION

This application is a continuation in part of my prior filed application Ser. No. 675,242, filed Apr. 8, 1976, now abandoned.

THE INVENTION - IN GENERAL

The present invention relates to improvements in parenteral fluid adminstration sets generally of the type disclosed in my prior application Ser. No. 608,576 filed Aug. 28, 1975, (now U.S. Pat. No. 3,949,745 dated Apr. 13, 1976) being characterized by a floating siphon operating within the chamber defined by a plastic-walled closed-ended cylindrical regulator having an upright open-ended overflow tube affixed to and extending upwardly from the bottom-end closure thereof and through which the longer leg of the siphon extends and through which, upon the siphon being suitably primed, fluid in controlled amount flows in droplet form to an IV tubing line extending to an infusion needle.

While parenteral fluid administration sets constructed and operating according to my aforesaid U.S. Pat. No. 3,949,745 are fully effective and well serve the purpose for which they were designed, recently it was learned that less cumbersome and simpler means to prime the siphon tube of the floating siphon, as initiates fluid flow therethrough, than that according to my aforesaid patent was not only very desirable but also was possible of attainment.

OBJECTS OF THE INVENTION

A principal object of the present invention, therefore, is the provision of a clinically acceptable and highly effective parenteral fluid adminstration set characterized by a floating-siphon type flow regulator means operating on the principle of the floating-siphon flow regulating means disclosed in my aforesaid U.S. Pat. No. 3,949,745 but which possesses the advantage thereover of being more simply and readily primed so as to initiate flow through the siphon tube, than the siphon means according to my patent aforesaid.

Another important object of the present invention is the provision of a floating siphon-type parenteral fluid flow regulator operating on the principle of the floating-siphon flow regulating means according to my aforesaid U.S. Pat. No. 3,949,745, but wherein the longer leg of the siphon U-tube has affixed thereto simple means normally disposed well above but aligned with the open-top of the overflow tube, for closing off same to air flow downwardly therethrough, as is a requisite to rendering the siphon operational.

Yet a further object of the invention is the provision of a parenteral fluid administration set employing a floating siphon-type flow regulator whose principle of operation is such that it may utilize a fluid-weightable float, a non-fluid weighted float, or a conventional float as per my prior U.S. Pat. No. 3,949,745, as the float component of the floating siphon thereof.

Yet another object of the invention is the provision of a parenteral fluid administration set as last aforesaid which according to one embodiment thereof utilizes a novel form and configuration of the float component of the floating siphon; i.e., a float having annular open-top cup configuration whose level in the body of the fluid in the regulator chamber is determined by the quantity of fluid admitted to the annular open-top cup portion of the float.

Still another object of the invention is the provision of an improved floating siphon-type parenteral fluid adminstration set wherein the level of the float element of the floating siphon in the body of fluid in the regulator chamber may be varied at will by the admission thereto of fluid from the fluid source, conventionally an inverted bottle, which effects weighting of said float as thereby varies its vertical height position in said chamber.

Figure 2:
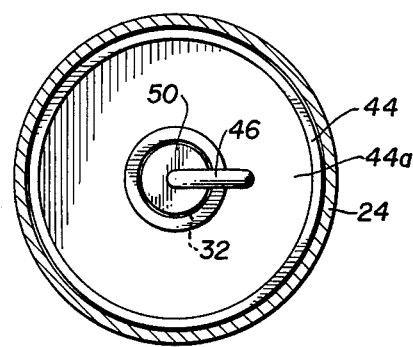

The above and other objects of the invention will become apparent from a consideration of the appended illustrative drawing figures and detailed description thereof, wherein:

FIG. 1 is a view in elevation, partly in section, illustrating an improved parenteral fluid administration set of the present invention which employs a fluid-weightable float as the float component of the floating siphon thereof, the view also illustrating in full lines the approximate lowermost position which the float and the U-tube components may assume and in broken lines the various positions which said float and U-tube components may take, and also the preferred configuration of the means affixed to the longer leg of the siphon tube for closing off the overflow tube to downward air flow therethrough shown in the operative position of the latter;

FIG. 2 is a section taken through the flow regulator of FIG. 1 on a horizontal plane thereof designated 2—2; and FIGS. 3 and 4 are similar views illustrative of a different form which the float component of the floating siphon may take, said float component being shown in the same relative positions as the float component of the FIG. 1 form.

Referring now to the drawing figures in detail, reference numeral 10 designates the neck end of an intravenous fluid-supply or reservoir bottle mounted (usually suspended) in inverted position and with its neck opening closed as by a cap 14 but with said cap shown to have been pierced by the point of a more or less conventional piercing plug 14 schematically shown to be provided with a capped, one-way filtered air in-flow passage 16 and an angled fluid outflow passage 18, 18a, to which latter is connected the stem of a branched i.e. Y-type, fitting 20 to one arm of which is connected a tube 22 shown as extending generally downward along the side of a plastic-walled, generally cylindrical flow regulator 24 and being connected thereinto at its lower end via a fitting 26 affixed to and opening into the lower end of the regulator chamber.

To the other arm of the branched Y fitting 20 is connected a short length of tubing 28 adapted to pass a limited amount of fluid from the bottle source to the interior of the regulator chamber via a tubular fitting 30 shown to extend through the top end closure 24a of the regulator chamber, upon said tubing being maintained in openflow condition. Fluid flow through said tubes 22, 28 may be controlled as by the clamp valves 22a, 28a respectively, affixed thereto as shown, although other suitable valve forms may be substituted.

Preferably, the flow regulator 24 is fashioned from a preferably clear resilient-plastic sheet shaped to the form of an elongate, uprightly disposed, cylindrical fluid container provided with said top-end closure 24a to which the piercing plug 14 may be affixed as shown (or formed integral therewith) and a bottom-end-closure wall 24b from which extends in fixed relation thereto an upright, open-top, open-bottom tube 32 functioning as an overflow tube or pipe. Thus, fluid from the bottle 10 admitted to the chamber provided by the cylindrical regulator as through said tube 22 and said fitting 26 may in theory collect in the lower end of said chamber until it reaches the open top of the upright overflow tube 32, whereupon any overflow occurring will pass downwardly through the tube to a lower-level elongate (also plastic-walled) receiving reservoir 34 shown to have substantially less diameter than that of the main cylindrical regulator 24 from which it depends. Illustratively, said receiving reservoir 34 is disposed coaxially with both said cylindrical regulating chamber 24 and said uprightly disposed overflow tube 32 and terminates at its lower end in a tapering end portion 34a delivering to an IV tubing line 36 under the control of a spherical ball valve 38, which in turn terminates in an infusion needle 40, all as disclosed in my aforesaid U.S. Pat. No. 3,949,745.

Disposed within the upright cylindrical regulator chamber 24 is a floating siphon assembly generally designated 42, the float component 44 of which, according to the form of float illustrated in FIG. 1, has annular open-top cup form, being disposed concentric with the upright overflow tube 32 and through whose central opening said overflow tube 32 extends, said float component being thus capable, when unweighted by fluid admitted to its interior, of riding on the surface of any substantial body of intravenous fluid from the bottle source of supply thereof admitted to the lower end of the regulator chamber via the tube 22 and fitting 26, to upper positions generally indicated in broken lines.

The floating siphon assembly 42 also incorporates a siphon U-tube 46 whose vertical position within the regulator chamber is determined by that of the float, the shorter leg 46a of which extends a small distance through and is affixed to the bottom-end wall of said float component 44 and whose longer leg 46b extends downwardly from the U of said U-tube through the bore of the upright overflow tube 34, preferably having length such that its lower end 48 always projects slightly below the bottom of the regulator chamber, for a purpose which will be hereafter explained.

According to a further feature of the invention, said longer leg 46b of the siphon U-tube has affixed thereto at a predetermined level above that of the open top of the overflow tube 32, a preferably truncated cone-shaped disc 50 of a size capable of serving as a closure for the open top 32a of the overflow tube 32 when moved downwardly into engagement therewith.

Although as previously stated, the upper end of the overflow tube 32 is normally open, upon weighting of the float component 44 of the floatingsiphon assembly as by fluid from the bottle source 10 supplied via the tubing 28 and fitting 30 to and collecting in the cup-shaped interior space thereof, the siphon tube 46b and the conically sectioned disc 50 lower in unison to respective positions in which said disc 50 seats snugly against the top open end 32a of the overflow tube 32, the edge of which is shown to be reversely coned or beveled so that it conforms to the coned under surface of the disc 50 whereby snug seating of disc on said open end is assured.

In operation of the FIG. 1 embodiment of fluid regulator and associated parts as just described, clamp valve 28a is first actuated to an open or partially open position thereby to admit fluid from the bottle supply 10 via the fitting 30 to the annular cup-shaped interior of the float 44 in amount partially filling same, thereby weighting the float whereupon said clamp valve 28a is again closed.

Clamp valve 22a which has been closed up to this point is now opened to admit a limited quantity of fluid via tubing 22 and fitting 26 into the lower end of the flow regulator chamber which is not enough to float the fluid-weighted float 44, with the result that said float assumes a position in which the flattened cone-shaped disc 50 affixed to the U-tube leg is disposed against the open-top of the upright overflow tube 32, thereby closing off said open-top end to air flow downwardly therethrough.

Hand-or finger-squeeze pressure now applied to usually opposite portions of the plastic-walled regulator 24 will substantially raise the pressure within the regulator chamber, as valve 28a has closed the branch line 28 to any reverse air flow therethrough and further as air flow through air-lock preventing valve 16a conventionally provided in the regulator side wall is one-way inward only. As a result of such pressure rise, the fluid in the regulator chamber below the float will be forced upwardly through the shorter siphon leg and thence downwardly through the longer leg of said siphon tube, finally exiting in drops from the regulator chamber through the lower end 48 of said longer leg 46b which extends into the reservoir extension 34, thus rendering the siphon operational.

Following application of hand or squeeze pressure to the opposite sides of the plastic-walled flow regulator, such pressure should be released slowly, thus to allow air to enter via the one-way inward valve 16a in amount replacing the fluid which has been forced through the siphon.

Upon the siphon becoming operational as aforesaid, as evidenced by fluid dropping from its longer arm whose outlet is below its intake, replacement fluid is then supplied to the chamber of regulator 24 via tubing 22 (clamp valve 22a being open) to bring fluid level in regulator chamber 24 up to that required to raise float 44 to near the level of the open top-end of the overflow tube 32. Clamp valve 22a is then adjusted to maintain the float at or near a steady level thereat.

As fluid continues to flow in drops into the collecting reservoir 34, clamp valves 52, 54 are opened and the I.V. tubing 36 is manipulated, i.e., raised and lowered, to allow fluid to flow into said tubing, thus expelling air bubbles and accomulating fluid in said collecting reservoir 34 to a level suspending (floating) the floating ball (sphere) valve 38; at this point, clamp valves 52, 54 may be closed and the needle 40 inserted into the patients vein. Clamp valve 54 is then adjusted to maintain fluid level in the receiving reservoir 34, such as to keep the floating sphere (valve) 38 afloat, it being explained that such requires little adjustment so long as the patient's vein remain clear.

However, in the even the vein becomes obstructed, fluid will back up into the reservoir chamber 34 and overflow tube 32, with the result that the siphon will cease to be operational upon the backed-up fluid in overflow tube reaching a level paralleling that having accumulated in the flow regulator chamber 24.

At this point, the infusion needle 40 may be manipulated to restore adequate flow or clamp valve 54 may be closed and the needle reinserted into another vein. In any case, when either of these expedients has brought about the desired result, and said clamp valve 54 is again opened, the system will resume uniform flow without further priming of the siphon being required.

An unique feature of the invention is that the annular cupshaped float 44 may be emptied simply by inverting the flow regulator. Thus, free of the weight of the fluid previously contained therein, said unweighted float will position itself only slightly submerged in the fluid body within the regulator chamber. It is to be understood however that the addition of fluid to the interior the cup-float, as adds a degree of weight thereto which lowers the siphon relative to the fluid level in the regulator chamber 24, is a feature which may be utilized to increase to a corresponding degree the rate of flow through the siphon.

When however a constant uniform rate of flow of a fluid of uniform viscosity without variation is desired, it follows that the aforesaid function of the annular cup-shaped open-top float component according to FIGS. 1 and 2, aside from variation in rate of flow, may be supplied equally well by a floating siphon employing a float of conventional make-up as employed in my aforeside U.S. Pat. No. 3,949,745.

More particularly, and now referring to FIGS. 3 and 4 which correspond generally with the previously described FIGS. 1 and 2, but which substitute for the float 44 thereof a float 60 of conventional construction, i.e., an annular float of buoyant, floatable material capable of riding on the surface of any body of intravenous fluid collecting in the lower end of resilient plastic-walled regulating chamber corresponding to the aforesaid regulator chamber 24, which fluid may be supplied thereto thru either (but not both) of the inlet nipples 30a, 26a, or by the means 18, 18a as disclosed in my aforesaid U.S. Pat. No. 3,949,745.

As with the FIGS. 1 and 2 illustrated form, the longer leg of the siphon tube 62 has affixed thereto normally at a pretermined distance or level above that of the open top of the overflow tube 64 a cone-shaped disc 66 (corresponding to the disc 50 of the FIGS. 1 and 2 form) which is adapted snugly to seat on the open top end of the said upright over flow tube 64, thereby to close off said open top end of the tube to air flow downwardly therethrough for priming purposes all as previously described. Following priming of the siphon and the siphon thereupon becoming operational, replacement fluid is supplied to the regulator chamber to bring the fluid level therein up to that required to raise the float to near the level of the open top-end of said over-flow tube 64, whereupon the same operation and/or operational steps as were previously described in connection with the FIGS. 1 and 2 form are followed, with the same advantageous results.

Without further analysis, it will be appreciated that the improvements above described for a parenteral fluid administration set of the general character disclosed and claimed in my aforementioned U.S. Pat. No. 3,949,745 dated Apr. 13, 1976 achieve the desirable objectives of the present invention as set forth in the foregoing. However, it will be understood that the invention is not limited to the precise constructional details which have been illustrated and described.

Having thus disclosed my improved parenteral fluid administration set according to the present invention, I make the following claims therefor:

I claim:

1. A parenteral fluid administration set comprising a source of supply of the fluid to be administered, a flow regulator to which fluid flows through a flow line from said source by gravity, said flow regulator comprising an upright plastic-walled cylinder having top-and-bottom-end walls providing a regulator chamber, a normally open-ended overflow tube affixed to the bottom end-wall of the regulator chamber and extending uprightly therein, the upper end of said overflow tube determining the maxium level of fluid permitted to collect in the regulator chamber, a floating siphon including an annular float and a siphon U-tube disposed in and being movable vertically within said regulator chamber in accordance with fluid level therein, means for supplying fluid from said source to the regulator chamber thereby to provide therein a body of fluid on which the float is adapted to float, said siphon U-tube being affixed to the float so as to be movable in unison therewith, the shorter leg of the siphon extending downwardly through the float and having its end open to the fluid body below the float, the longer leg of the siphon extending downwardly through the bore of said upright over-flow tube and having affixed thereto at a predetermined position along its length which normally is well above the open-top of the overflow tube a disc-form valve element which is adapted to lower against and seat on said open top of the overflow tube thereby to close said overflow tube to downward-outward air flow therethrough responsive to manually induced build-up of air pressure within said regulator chamber, said presure build-up also functioning to prime the siphon.

2. A parenteral fluid administration set according to claim 1, wherein said annular float is fluid-weightable, and wherein means are provided to supply weighting fluid thereto from said source.

3. A parenteral fluid administration set according to claim 1, wherein said annular float is fashioned from buoyant, floatable material whereby it is adapted to ride on any body of fluid present to said regulator chamber.

4. A parenteral fluid administration set according to claim 2 wherein separate valve controlled fluid-flow lines extending between the source of fluid and the top-end wall of the flow regulator and between the said source and the lower end of the cylindrical wall of the flow regulator are provided.

5. A parenteral fluid administration set according to claim 4, wherein the longer leg of the siphon terminates below the cylindrical regulator bottom-end wall and has affixed thereto adjacent its end means for altering the bore of the siphon outlet in accordance with the viscosity of the fluid being administered.

6. A parenteral fluid administration set according to claim 3, wherein the longer leg of the siphon terminates below the cylindrical regulator bottom-end wall and fluid exits from its open end in droplet form at a substantially constant rate.

7. A parenteral fluid administration set according to claim 6 wherein the longer leg of the siphon extends below the cylindrical regulator bottom-end wall and terminates in a reservoir depending from said end wall.

8. A parenteral fluid administration set according to claim 1, wherein said plastic-walled cylinder is fashioned of resilient plastic whereby manually induced build-up of air pressure is effected by hand-squeeze pressure applied to diametrically opposed wall areas of said plasticwalled cylinder.

9. A parenteral fluid administration set according to claim 1, wherein said disc-form valve element and the open top of overflow tube against which said valve element seats are complementally shaped to insure effective seating of the valve on said top.

10. A parenteral fluid administration set comprising a source of supply of the fluid to be administered, a flow regulator to which fluid flows through a flow line from said source by gravity, said flow regulator comprising an upright plastic-walled cylinder having top-and bottom-end walls together providing a regulator chamber, a normally open-ended overflow tube affixed to the bottom end-wall of the regulator chamber and extending uprightly therein, the upper end of said overflow tube determining the maximum level of fluid permitted to collect in the regulator chamber, a floating siphon including an annular float and a siphon U-tube disposed in and being movable vertically within said regulator chamber in accordance with fluid level therein, valved means for supplying fluid from said source to the lower end of the regulator chamber thereby to provide therein a body of fluid on which the float is adapted to float, and means for priming the siphon including a disc-form valve element affixed to the longer siphon leg in position along its length which normally is well above the open top of the overflow tube but which lowers against said open to responsive to increase of air pressure within the regulator chamber induced by squeeze pressure manually applied to the plastic wall of the regulator chamber, thereby forcing the fluid in the lower end of said chamber below the float to flow upwardly through the shorter leg and thence downwardly through and from the end of longer leg of the siphon U-tube.

* * * * *